(12) United States Patent
Gandhi

(10) Patent No.: US 11,883,271 B2
(45) Date of Patent: Jan. 30, 2024

(54) MEDICATION KIT

(71) Applicant: Ashwin Gandhi, Oakville (CA)

(72) Inventor: Ashwin Gandhi, Oakville (CA)

( * ) Notice: Subject to any disclaimer, the term of this patent is extended or adjusted under 35 U.S.C. 154(b) by 0 days.

(21) Appl. No.: 17/998,015

(22) PCT Filed: Jul. 14, 2020

(86) PCT No.: PCT/CA2020/050978
§ 371 (c)(1),
(2) Date: Nov. 4, 2022

(87) PCT Pub. No.: WO2022/011447
PCT Pub. Date: Jan. 20, 2022

(65) Prior Publication Data
US 2023/0172772 A1 Jun. 8, 2023

(51) Int. Cl.
*A61J 1/03* (2023.01)
*A61F 17/00* (2006.01)
*A61J 1/16* (2023.01)

(52) U.S. Cl.
CPC ................ *A61F 17/00* (2013.01); *A61J 1/16* (2013.01); *A61J 2205/30* (2013.01)

(58) Field of Classification Search
CPC ........ A61J 2205/30; A61J 7/04; A61J 7/0084; A61J 1/03; B65D 2203/00; B65D 21/0204; B65D 75/327; B65D 2221/00; B65D 2205/30; B65D 1/035; B65D 7/04; B65D 7/0084; B65D 83/0409; B65D 83/0481; B65D 2251/1066; B65D 43/164

USPC ............ 206/459.5, 531, 539, 534, 232, 570
See application file for complete search history.

(56) References Cited

U.S. PATENT DOCUMENTS

| | | | |
|---|---|---|---|
| 6,571,955 B1* | 6/2003 | Rossman | B65D 85/20 206/538 |
| 2008/0215440 A1* | 9/2008 | Peterson | B65D 77/046 53/473 |
| 2009/0230013 A1* | 9/2009 | Born | A61J 7/0084 206/534 |
| 2009/0230015 A1* | 9/2009 | Harrison | B65D 21/0204 220/737 |

OTHER PUBLICATIONS

International Search Report, dated Mar. 18, 2021 for corresponding International Application No. PCT/CA2020/050978 (3 pages).
Written Opinion of the ISA, dated Mar. 18, 2021 for corresponding International Application No. PCT/CA2020/050978 (3 pages).

* cited by examiner

*Primary Examiner* — King M Chu
(74) *Attorney, Agent, or Firm* — Intellectual Property Law Group LLP

(57) ABSTRACT

A medication kit for treating a health condition of a patient is provided. The medication kit includes a plurality of medicinal agents for treating a plurality of symptoms associated with the health condition. Each of the plurality of medicinal agents is adapted to treat one or more symptoms out of the plurality of symptoms. The medication kit further includes a plurality of containers for storing the plurality of medicinal agents. Each container stores one of the plurality of the medicinal agents.

15 Claims, 3 Drawing Sheets

MEDICATION KIT

CROSS-REFERENCE TO RELATED APPLICATION

This application is a U.S. National Phase application, under 35 U.S.C. § 371, of International Application no. PCT/CA2020/050978, filed on Jul. 14, 2020, which is hereby incorporated by reference for all purposes.

TECHNICAL FIELD

The present disclosure relates, generally, to a medication kit, and more particularly relates to a pre-packaged medication having a plurality of medicinal agents in dosage form for the treatment of one or more symptoms.

BACKGROUND

Various types of multi-symptom medicines are known in the art and are currently marketed over the counter for temporarily treating symptoms caused by the common cold, flu, allergies, or other breathing illnesses (such as sinusitis, bronchitis). These types of minor illnesses don't typically exhibit just one symptom, therefore there are times when it may be more convenient to take one single medication that treats multiple symptoms.

A major draw-back of some of the current all-in-one, multi-symptom medications is that often, for the sake of convenience, a patient ends up needlessly ingesting medications meant to treat symptoms that the patient may not exhibit. Health care practitioners generally recommend that, if a patient does not have a particular symptom, there is no need to treat that symptom. Taking a multi-symptom medication that treats symptoms which a user does not have is not only a waste, but it can cause unnecessary side effects and may sometimes be dangerous.

Health-care practitioners also advise patients to avoid taking multiple medications that may contain the same or similar ingredients, because this can (and frequently does) lead to an overdose. One common ingredient that requires utmost attention (to avoid overdosing) is acetaminophen, which is included in many multi-symptom cold and flu medications. Additionally, patients often take additional acetaminophen doses to reduce their fever or aches and pains, not realizing that they're taking more than needed. Taking too much acetaminophen can be life threatening and can lead to liver failure.

Single-symptom medications (addressing each particular symptom associated with a health condition, such as, cold and flu) are also known in the art and are commonly sold over-the-counter. In principle, a perfectly informed and educated pharmacy-shopper, given enough time, could pick up just those single-symptom cold and flu medications that strictly correspond to the actual symptoms experienced, thus avoiding the taking of unneeded medicines. However, very few shoppers are sufficiently informed and educated and have the time to confidently make such treatment selection from the dizzying array of over-the-counter single-symptom medications displayed at a typical pharmacy. Furthermore, there exists a large variation in the number of doses included within each package of such single-symptom medications, which often results in mismatches and wasteful buying (e.g. by having leftover medicine at the end of the treatment, which will likely be not used again before the expiration date).

SUMMARY

In accordance with one embodiment of the present disclosure, a medication kit for treating a health condition of a patient is provided. The medication kit includes a plurality of medicinal agents for treating a plurality of symptoms associated with the health condition. Each of the plurality of medicinal agents is adapted to treat one or more symptoms out of the plurality of symptoms. The medication kit further includes a plurality of containers for storing the plurality of medicinal agents. Each container stores one of the plurality of the medicinal agents.

In accordance with another embodiment of the present disclosure a medication kit for treating a health condition of a patient is provided. The medication kit includes a plurality of medicinal agents for treating a plurality of symptoms associated with the health condition. Each of the plurality of medicinal agents is adapted to treat one or more symptoms out of the plurality of symptoms. The medication kit further includes a plurality of containers for storing the plurality of medicinal agents. Each container stores one of the plurality of the medicinal agents. The medication kit also includes a plurality of indicia arranged on the plurality of containers. The plurality of indicia facilitates in identifying the plurality of medicinal agents stored inside the plurality of containers.

DETAILED DESCRIPTION

Figure 1:
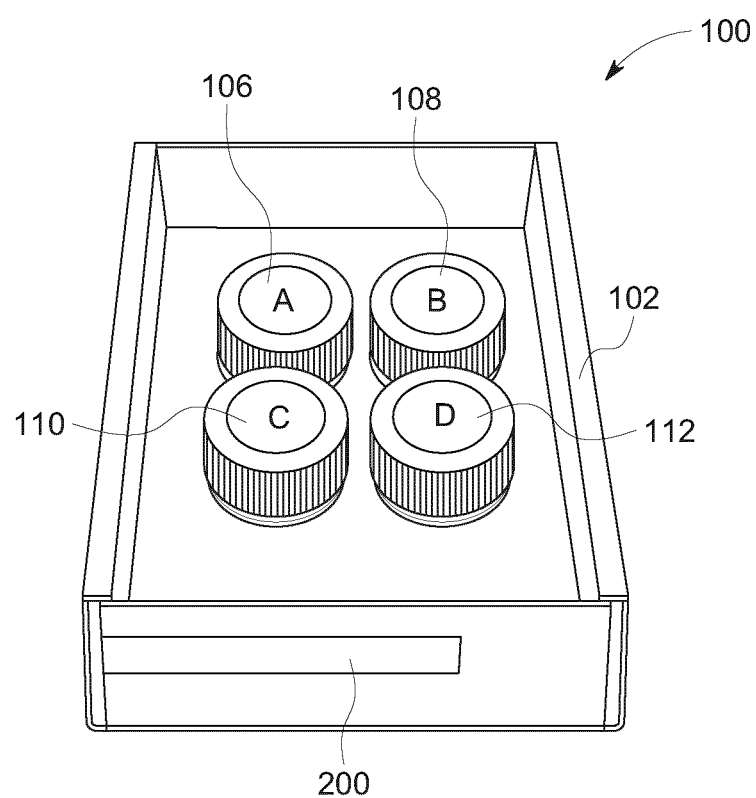
FIG. 1 illustrates a perspective view of a medication kit having a plurality of containers, in accordance with an embodiment of the disclosure.

In the following description, for purposes of explanation, numerous specific details are set forth in order to provide a thorough understanding of the present disclosure. It will be apparent, however, to one skilled in the art that the present disclosure can be practiced without these specific details. In other instances, apparatus and methods are shown in block diagram form only in order to avoid obscuring the present disclosure.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Further, the terms "a" and "an" herein do not denote a limitation of quantity, but rather denote the presence of at least one of the referenced items. Moreover, various features are described which may be exhibited by some embodiments and not by others. Similarly, various requirements are described which may be requirements for some embodiments but not for other embodiments.

Some embodiments of the present disclosure will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. The use of any term should not be taken to limit the spirit and scope of embodiments of the present invention.

The embodiments are described herein for illustrative purposes and are subject to many variations. It is understood that various omissions and substitutions of equivalents are contemplated as circumstances may suggest or render expedient but are intended to cover the application or implementation without departing from the spirit or the scope of the present disclosure. Further, it is to be understood that the phraseology and terminology employed herein are for the purpose of the description and should not be regarded as limiting. Any heading utilized within this description is for convenience only and has no legal or limiting effect.

Figure 2:
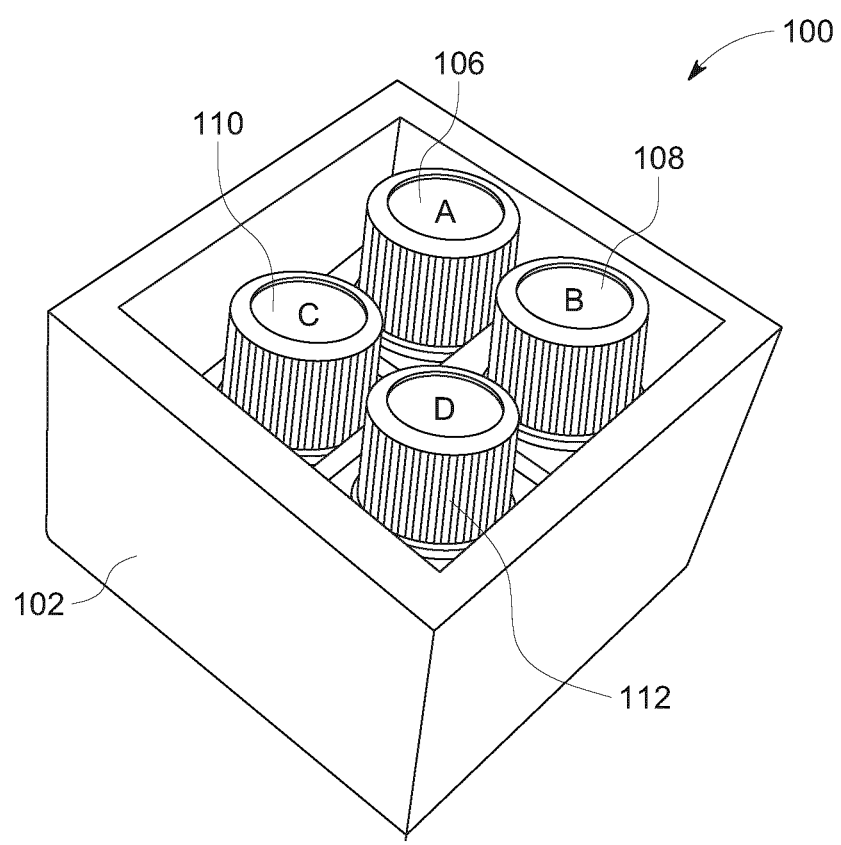
FIG. 2 illustrates a perspective view of a medication kit depicting a housing and a plurality of containers arranged inside the housing, in accordance with an embodiment of the disclosure.

Referring to FIG. 1 and FIG. 2, a medication kit 100 for treating a plurality of symptoms associated with a health condition is shown. As shown, the medication kit 100 may include a housing 102, such as a box, and a plurality of containers, for example, a first container 106, a second container 108, a third container 110, and a fourth container 112, disposed inside the housing 102. Although, the medication kit 100 is shown to include four containers, it may be appreciated that the medication kit 100 may include any number of containers depending on various symptoms experienced by a patient for a health condition. Although, the medication kit 100 having the housing 102 for storing the containers 106, 108, 110, 112 is shown and contemplated, it may be appreciated that the housing 102 may be omitted. In such a case, the plurality of containers 106, 108, 110, 112 may be wrapped together by using a tape or a wrapper film to form the kit.

Further, the medication kit 100 includes a plurality of medicinal agents stored inside the plurality of containers. Preferably, each of the plurality of container stores an individual medicinal agent (also referred to as medication) out of the plurality of medicinal agents in a dosage form for addressing a specific symptom. For example, the first container 106 may include a dosage form comprising an analgesic formulation (pain reliever), the second container 108 may include a dosage form comprising a fever relief formulation, a third container 110 may include a dosage form comprising a decongestant formulation, and the fourth container 112 may include a dosage form comprising an expectorant formulation. In some implementations, the medication kit 100 may include additional containers for containing a dosage form comprising an antihistamine (anti-allergy) formulation, a dosage form comprising an antitussive formulation (cough suppressant), a dosage form comprising a nasal spray decongestant formulation, a dosage form comprising a throat anesthetic formulation. It may be appreciated that the formulations listed above are exemplary formulations and the medication kit 100 may include any other additional dosage form corresponding to any other symptoms. Also, the medication kit 100 may include any combination of formulations to treat any combination of symptoms.

By way of example (and not intended to be an exhaustive list), each of the respective formulations listed in the paragraph above may be as follows:

analgesic formulation: ibuprofen, acetaminophen, acetylsalicylic acid, naproxen, COX-1 and/or COX-2 inhibitors, etc.

fever relief formulation: ibuprofen, acetaminophen, acetylsalicylic acid, etc.

"decongestant formulation" and "nasal spray decongestant formulation": phenylephrine, oxymetazoline, ephedrine, epinephrine, phenylpropanolamine, pseudoephedrine etc.

expectorant formulation: Guaifenesin, etc.

antihistamine (anti-allergy) formulation: chlorpheniramine, cetirizine, loratadine, desloratadine, cromolyn sodium, doxylamine succinate, etc.

antitussive formulation: dextromethorphan, codeine, etc.

throat anesthetic formulation: dyclonine, benzocaine, etc.

Further, the medication kit 100 includes a plurality of identification indicia affixed to the plurality of containers to facilitate in identification of the medication and the dosage of the medication stored in each of the plurality of containers 106, 108, 110, 112. It may be appreciated that each of the plurality of containers 106, 108, 110, 112 is affixed with different identification indicia depending on the medication and the dosage of the medication. For example, the first container 106 is affixed with an indium A, the second container 108 is affixed with an indicium B, the third container 110 is affixed with an indicium C, and the fourth container 112 is affixed with indicium D. In an embodiment, each indicium may be affixed on a lid of a corresponding container. Additionally, the indicium may be affixed to the sides of each individual container. In some embodiments, various containers within the medication kit 100 might bear different identification indicia, such as E, AH, DM, D(s), etc. In an embodiment, each indicium is selected and assigned part based on a common abbreviation for the particular medicine (or the class of medicine) stored/disposed in each container 106, 108, 110, 112. For example, the individual containers 106, 108, 110, 112 may be preferably labelled according to the following convention:

A for Acetaminophen;
B for iBuprofen;
C for Cetirizine;
D for Decongestant
D(S) for Decongestant spray;
E for Expectorant;
DM for Dextromethorphan; and
AH for Anti-Histamine.

The labelling of indicium on each of the containers 106, 108, 110, 112 also facilitates a repurchase of a single medicine of the medication kit 100 by the patient. For so doing, the patient may purchase an individual replacement container of that medicine, simply by returning to the pharmacy, and requesting to buy a replacement for only the container bearing the particular indicium. For example, the patient may ask the pharmacist for the replacement of the container 106 having the indicium A, or the container 108 having the indicium D, etc. Therefore, the plurality of indicia ensures consistency, simplicity, and accuracy in the process of buying medicine refills for the medication kit 100.

In an embodiment, the housing 102 may include a box-like configuration or tray-like configuration suitable for retail display to allow a potential buyer to see the plurality of containers 106, 108, 110, 112 arranged inside, and to see the identification indicia affixed to each of the containers 106, 108, 110, 112. When the drug regulations mandate that a particular over-the-counter medicinal formulation, intended to be sold within the medication kit 100, is to be kept behind the pharmacist's counter and is to be handed out only by a licensed pharmacist, the present disclosure envisages that the housing 102 could be displayed on the selfserve pharmacy retail shelves with empty containers 106, 108, 110, 112 arranged inside the housing 102. For such configurations, the "empty" retail display kit will either be fitted with one or more "dummy" containers (which do not contain medicine), or such "empty" retail display kit could just be displayed without any contents, except for a placeholder message urging potential buyers to take the "empty" retail display kit to the pharmacist on duty, to have the containers with the real medicine placed inside the medication kit 100 for sale to the customer.

Various other information related to branding, contents and therapeutic indications may be printed or affixed to an outer surface of the housing 102. In some embodiments, the medication kit 100 also includes a printed instructions manual 200, such as, a leaflet, a drug insert, a product monograph and the like, are preferably placed inside the housing 102. The printed instruction manual 200 may include instructions for taking medicine, information regarding the medicine stored in each container and the associated dosage, information about individual medicine and/or combination of medicine to be ingested for any particular symptom or a combination of symptoms.

Figure 3:
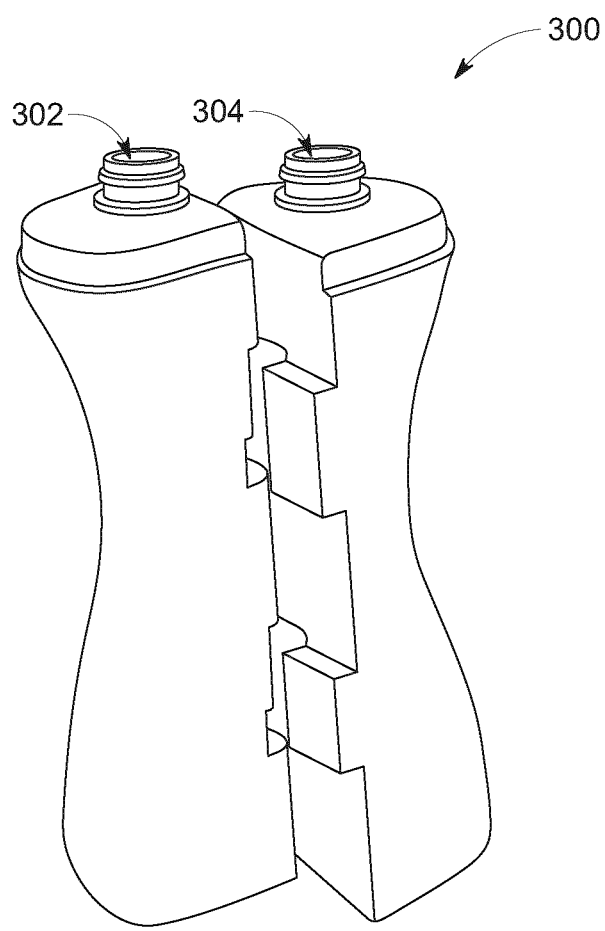
FIG. 3 illustrates a perspective view of a container having two chamber for storing medicinal liquid, in accordance with an embodiment of the disclosure.

In an embodiment, the medication kit 100 may include dosage of each medicine in regular strength, extra strength, and/or children version (low dosage). For the children's version of the medication kit 100, the medication kit 100 may comprise individual medicinal formulations in liquid (or syrup) form. In such a case, the individual containers 106, 108, 110, 112 of the medication kit 100 may be adapted to hold and dispense liquids and may include a spoon, pipette, or other suitable dose-measuring means. In an embodiment, as shown in FIG. 3, the one or more containers 300 may include two chambers 302, 304 for storing two medicinal formulation. The container 300 may include separate cap for facilitating an independent opening and closing of each of the chambers 302, 204. Accordingly, the container 300 enables independent dispensing of each medicinal liquid stored in the chambers 302, 204.

For marketing purposes, the medication kit 100 may be labeled as "Allergy and Sinus Kit", or "Cold, Flu and Sinus Kit", or "Head, Nose and Chest Kit", or any other combination of similar terms known in the art of marketing pharmaceutical formulations suitable for temporary treatment, prevention, or amelioration of symptoms caused by the common cold, flu, allergies, or other breathing illnesses (such as sinusitis, bronchitis, etc.). Depending on the type of individual medicinal formulations contained within the medication kit 100, the medication kit 100 may be respectively labeled as "Night Relief" or "Day Relief" or "Non-Drowsy". Special versions of the medication kit 100 may also be marketed as "Special Formulation For Patients With High Blood Pressure", in which case the individual medicines within such medication kit 100 will be of a type/class that is not counter indicated for patients with high blood pressure.

In a preferred embodiment of this invention, the medication kit 100 may be assigned a unique stock keeping unit (SKU) number for retail stock management purposes. In an embodiment, each of the plurality of containers 106, 108, 110, 112 may have its SKU number. The SKU number can be printed on the housing 102 and/or each of the containers 106, 108, 110, 112 as a machine-readable bar code. In an embodiment, the housing 102 and/or each of the containers 106, 108, 110, 112 may include RFID tags for identifying the respective medication kit 100 and/or the containers 106, 108, 110, 112. For drug regulatory purposes, the medication kit 100 may be assigned one unique drug identification number (DIN), or alternatively, each of the containers 106, 108, 110, 112 be assigned individual DIN according to the medicinal formulation contained inside each of the containers 106, 108, 110, 112.

Due to the convenient combination of two or more individual medicinal formulations within the medication kit, the present disclosure presents great advantages for those shoppers who wish to select and buy medicine to strictly treat only those actual symptoms experienced. The medication kit according to the present disclosure can also save money to the end user, by doing away with the need to wastefully buy too many kinds of single-symptom medicines or too many doses of each medicine. The medication kit 100 also removes the anxiety, the wasted time, and the information overload that previously would have been unavoidable if a shopper wanted to only treat those symptoms she actually experiences, by selecting and buying several single-symptom cold and flu medications on her own.

Further, the medication kit 100 will allow patients to take medication based on the symptoms patients has and use different medication as disease/symptoms changes. Also, contents of the medication kit can be changed to accommodate patient other medical conditions like with blood pressure or prostate problem. Choosing the right medication kit 100 with right ingredient will eliminate the chances of causing issue with patient's existing medical condition.

In an exemplary embodiment, the medication kit 100 may be an allergy Kit and may include various medicinal agents, which can be taken by a person based on his/her symptoms. For example, the person suffering from grass allergy may be fine with just taking one antihistamine a day but when neighbor is cutting the grass in the evening and the person is returning home that night, he or she may have flare up of allergy symptoms and may have additional symptoms of nasal congestion. In such a case, the person may take additional medicinal agent of the medication kit 100 to help alleviate the nasal congestion patient might have when exposed to higher allergen.

In an exemplary embodiment, the medication kit 100 may be a cold and cough Kit. In the common cold, symptoms usually progress from sore throat to runny and stuffy nose and eventually may cause dry or wet cough. The medication kit 100 may include various medicinal agents and allows a patient to choose the right medication agent(s) for the symptoms they have and change their medication agent as symptoms change without having to buy a plethora of different medication; saving money, time and avoiding side effects of unnecessary medication.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A medication kit for treating a health condition of a patient, the medication kit comprising:
   a plurality of medicinal agents for treating a plurality of symptoms associated with the health condition, wherein each of the plurality of medicinal agents is adapted to treat one or more symptoms out of the plurality of symptoms; and
   a plurality of containers for storing the plurality of medicinal agents, wherein each container stores at least one of the plurality of the medicinal agents;
   wherein at least one of the plurality of containers is configured to be divided into at least two chambers, each chamber having a separate opening from another chamber;
   wherein the at least two chambers of the at least one of the plurality of containers comprise: a first chamber and a second chamber, the first chamber being removably attachable to the second chamber by an interlocking connection along adjacent surfaces of the first and second chambers.

2. The medication kit of claim 1 further including a housing for storing the plurality of containers.

3. The medication kit of claim 1 further including a plurality of indicia arranged on the plurality of containers, wherein the plurality of indicia facilitates in identifying the plurality of medicinal agents stored inside the plurality of containers.

4. The medication kit of claim 3, wherein one indicium of the plurality of indicia corresponds to one medicinal agent.

5. The medication kit of claim 1 further including a leaflet containing information associated with the medicinal agent stored in each container, information related to associated dosage, information about individual medicine and/or combination of medicines to be ingested for any particular symptom or a combination of symptoms, or a combination thereof.

6. A medication kit for treating a health condition of a patient, the medication kit comprising:
   a plurality of medicinal agents, each adapted to treat one or more symptoms associated with cough, cold, allergy, flu or sinusitis; and
   a plurality of containers for storing the plurality of medicinal agents, wherein each container stores at least one of the plurality of the medicinal agents;
   wherein at least one of the plurality of containers is configured to be divided into at least two chambers, each chamber having a separate opening and each chamber holding a different medicinal agent than another chamber;
   wherein the at least two chambers of the at least one of the plurality of containers comprise: a first chamber and a second chamber, the first chamber being removably attachable to the second chamber by an interlocking connection along adjacent surfaces of the first and second chambers.

7. The medication kit according to claim 6, wherein the different medicinal agents in the at least two chambers of the at least one of the plurality of containers are effective to treat only one of the group of conditions consisting of cough, cold, allergy, flu and sinusitis.

8. The medication kit according to claim 6, wherein the different medicinal agent in one chamber is different from another chamber in terms of dosage strength of medication.

9. The medication kit according to claim 6, wherein the different medicinal agent in one chamber is different from another chamber in terms of day time and night time usage.

10. The medication kit according to claim 6, wherein each chamber is configured to store medicinal agent of different forms including liquid form and solid form.

11. The medication kit according to claim 6, wherein each chamber is configured to dispense medicinal agent independently from another chamber, each opening being independently closeable and openable.

12. The medication kit of claim 6, further including a housing for storing the plurality of containers.

13. The medication kit of claim 6, further including a plurality of indicia arranged on the plurality of containers, wherein the plurality of indicia facilitates in identifying the plurality of medicinal agents stored inside the plurality of containers.

14. The medication kit of claim 13, wherein one indicium of the plurality of indicia corresponds to one medicinal agent.

15. The medication kit of claim 6, further including a leaflet containing information associated with the medicinal agent stored in each container, information related to associated dosage, information about individual medicine and/or combination of medicines to be ingested for any particular symptom or a combination of symptoms, or a combination thereof.

* * * * *